(12) United States Patent
Mitchell (10) Patent No.: US 8,597,301 B2
(45) Date of Patent: Dec. 3, 2013

(54) CANNULA WITH LATERAL ACCESS AND DIRECTIONAL EXIT PORT

(76) Inventor: David Mitchell, Spartanburg, SC (US)

( * ) Notice: Subject to any disclaimer, the term of this patent is extended or adjusted under 35 U.S.C. 154(b) by 830 days.

(21) Appl. No.: 11/976,016

(22) Filed: Oct. 19, 2007

(65) Prior Publication Data

US 2009/0105711 A1 Apr. 23, 2009

(51) Int. Cl.
*A61B 17/58* (2006.01)
(52) U.S. Cl.
USPC .............................. 606/92; 606/86 R; 606/93
(58) Field of Classification Search
USPC ................................ 606/92–93; 600/566–567
See application file for complete search history.

(56) References Cited

U.S. PATENT DOCUMENTS

| | | | |
|---|---|---|---|
| 2,409,979 A | 3/1946 | Huber | |
| 4,488,549 A | 12/1984 | Lee et al. | |
| 4,513,754 A | 4/1985 | Lee | |
| 4,627,434 A | 12/1986 | Murray | |
| 4,654,314 A | 3/1987 | Takagi et al. | |
| 4,721,112 A | 1/1988 | Hirano et al. | |
| 4,842,585 A | 6/1989 | Witt | |
| 4,969,888 A | 11/1990 | Scholten et al. | |
| 5,007,932 A | 4/1991 | Bekki et al. | |
| 5,012,818 A | 5/1991 | Joishy | |
| 5,108,404 A | 4/1992 | Scholten et al. | |
| 5,192,282 A | 3/1993 | Draenert | |
| 5,192,283 A | 3/1993 | Ling et al. | |
| 5,360,441 A | 11/1994 | Otten | |
| 5,800,389 A * | 9/1998 | Burney et al. | 604/164.01 |
| 5,800,409 A | 9/1998 | Bruce | |
| 5,800,437 A | 9/1998 | Gustilo et al. | |
| 5,871,470 A * | 2/1999 | McWha | 604/158 |
| 6,024,730 A | 2/2000 | Pagan | |
| 6,033,411 A | 3/2000 | Preissman | |
| 6,120,494 A | 9/2000 | Jonkman | |
| 6,203,524 B1 * | 3/2001 | Burney et al. | 604/93.01 |
| 6,235,043 B1 | 5/2001 | Reiley et al. | |
| 6,440,138 B1 | 8/2002 | Reiley et al. | |
| 6,613,054 B2 | 9/2003 | Scribner et al. | |
| 6,673,068 B1 | 1/2004 | Berube | |
| 6,719,761 B1 | 4/2004 | Reiley et al. | |
| 6,726,691 B2 | 4/2004 | Osorio et al. | |
| 6,863,672 B2 | 3/2005 | Reiley et al. | |
| 6,875,219 B2 | 4/2005 | Arramon et al. | |
| 6,981,981 B2 | 1/2006 | Reiley et al. | |
| 7,027,873 B2 | 4/2006 | Pajunk et al. | |
| 7,704,256 B2 | 4/2010 | Sand et al. | |
| 7,771,431 B2 | 8/2010 | Scribner et al. | |

(Continued)

OTHER PUBLICATIONS

PCT/US 08/74344—PCT Notification of Transmittal of the International Search Report and the Written Opinion of the International Searching Authority, or the Declaration dated Nov. 6, 2008.

(Continued)

*Primary Examiner* — Nicholas Woodall
(74) *Attorney, Agent, or Firm* — Tarolli, Sundheim, Covell & Tummino LLP (57) ABSTRACT

The present invention generally provides a cannula system that is readily maneuverable in an operating room setting, can be used to expose different instrumentalities to a target site, and has directional capabilities to allow the user to treat multiple quadrants or areas of a target site. The present invention provides cannula systems including these different instrumentalities as well as methods of operating these cannula systems and methods of treating orthopedic conditions using these cannula systems.

24 Claims, 7 Drawing Sheets

(56) References Cited

U.S. PATENT DOCUMENTS

| | | |
|---|---|---|
| 7,887,543 B2 | 2/2011 | Sand et al. |
| 2002/0032447 A1 | 3/2002 | Weikel et al. |
| 2002/0099385 A1* | 7/2002 | Ralph et al. ............... 606/92 |
| 2003/0050702 A1* | 3/2003 | Berger ................. 623/17.12 |
| 2005/0124989 A1 | 6/2005 | Suddaby |
| 2006/0122625 A1 | 6/2006 | Truckai et al. |
| 2006/0276749 A1 | 12/2006 | Selmon et al. |
| 2007/0191858 A1 | 8/2007 | Truckai et al. |
| 2007/0233146 A1* | 10/2007 | Henniges et al. ........... 606/91 |
| 2008/0021463 A1 | 1/2008 | Georgy |
| 2008/0058827 A1 | 3/2008 | Osorio et al. |
| 2008/0086142 A1* | 4/2008 | Kohm et al. ............... 606/92 |
| 2008/0119821 A1* | 5/2008 | Agnihotri et al. ........... 604/513 |
| 2008/0255563 A1* | 10/2008 | Farr et al. ................. 606/79 |

OTHER PUBLICATIONS

PCT/US2008/074344, International Preliminary Report on Patentability dated Apr. 20, 2010.

* cited by examiner

CANNULA WITH LATERAL ACCESS AND DIRECTIONAL EXIT PORT

BACKGROUND OF THE INVENTION

There are many different orthopedic conditions that require surgical intervention. For example, bone fractures are a very common orthopedic problem that can occur because of a number of factors, such as injury, disease or progressive age. One type of surgical procedure used to treat fractures of the spine is vertebroplasty. Vertebroplasty involves injecting liquid bone cement into the interstices of the weakened bone under pressure. The bone cement subsequently hardens to fix the vertebral body. Another process is kyphoplasty, in which a mechanical bone tamping device is used to elevate the vertebral body. An orthopedic cement is then injected into the space created by the bone tamp. Specifically, a bone tamping device, such as a balloon, can be placed into the intervertebral body and inflated so that a cavity is formed in the weakened bone. This cavity can then be filled with a more viscous form of bone cement.

Another type of orthopedic condition is degenerative disc disease, which can involve degeneration and age-related changes in the macroscopic, histologic and biochemical composition and structure of the annulus fibrosus and/or the nucleus pulposus of an intervertebral disc. There are numerous surgical treatment options for painful degenerative disc disease that have ranged in the past from interbody fusions to total disc replacement. Another, more recent option is plasma disc decompression which involves removing tissue from the nucleus pulposus using low temperature plasma excision.

Many of the orthopedic tools used in these procedures and other orthopedic procedures involve complex, high profile components. In addition, many are not completely controllable by the user. For example, in balloon kyphoplasty the balloons used to create the cavity can expand along the path of least resistance forming an unusual or asymmetrical cavity which inhibits or compromises the ideal placement of the cement. Therefore, the dimensions of a balloon created cavity are largely beyond the control of the user and more or less dependent upon the extent of disruption of the architecture of the pathologic bone. Furthermore, a problem associated with current orthopedic tool placement systems used in many of these procedures is that they do not accommodate the vertical height limitations present in the operating room during the procedure. For example, because of the fluoroscopic imaging devices that are above the orthopedic tool placement systems, a user has limited vertical space to maneuver instruments through the tool placement systems.

Therefore, a more controllable, lower profile orthopedic tool and accompanying placement system that is also designed to accommodate the user during performance of the surgical procedure is needed.

SUMMARY OF THE INVENTION

In an embodiment, the present invention provides a cannula system that allows for directional placement of an orthopedic tool as well as a side entry port that provides a user with more maneuverability in handling the orthopedic tool during a surgical procedure. A cannula of a cannula system of the present invention generally comprises a handle and a cannula shaft. The handle comprises a handle body having a proximal portion and a distal portion. The cannula shaft comprises an elongate tubular body having a proximal end depending from the distal portion of the handle body, a distal end terminating in a pointed tip, and a longitudinal axis extending therethrough. The handle further comprises a first side entry port in fluid communication with a first lumen that has at least a partial section that is curved or angled with respect to an imaginary center line that extends through the handle body. The imaginary center line is also aligned with the longitudinal axis of the cannula shaft. The cannula shaft further has an inner wall defining a channel that has a proximal end and a distal end. The proximal end of the channel is in fluid communication with the first lumen of the handle body and the distal end of the channel is in fluid communication with a side distal exit port. The distal end of the channel is also spaced apart from the distal end of the elongate body. The inner wall is configured to laterally deflect the channel at the channel's distal end with respect to the longitudinal axis of the elongate body to transition the channel's distal end to the side distal exit port.

The present invention also provides a method of using this embodiment of a cannula system to treat an orthopedic condition that involves a target site in the body. Such a method comprises inserting an orthopedic tool in the first side entry port of the handle, urging the orthopedic tool down the first lumen of the handle and then the channel of the cannula shaft and then urging the orthopedic tool through the side distal exit port to access one portion of the target site in the body. Once the orthopedic tool has exited the side distal exit port, the method comprises performing a surgical function on the one portion of the target site. In certain embodiments, only one portion of the target site may need to be treated. However, in other embodiments, it may be desirable to treat another portion of the target site. In such embodiments, the method further comprises removing the orthopedic tool from the cannula, and rotating the cannula such that the side distal exit port faces the another portion of the target site. The method further comprises urging the orthopedic tool down the first lumen of the handle and then the channel of the channel shaft and then urging the orthopedic tool through the side distal exit port to access the another portion of the target site. Once the orthopedic tool has exited the side distal exit port, the method further comprises performing a surgical function on the another portion of the target site. This process can be repeated on as many different portions of the target site as necessary. The orthopedic tool can then be removed from the patient along with the cannula. In a preferred embodiment, the orthopedic tool is a bone tamp, the target site is a vertebral fracture, and the surgical function is tamping bone.

In another embodiment, the present invention provides a cannula system including a cannula that comprises a handle and a cannula shaft. The handle comprises a handle body having a proximal portion and a distal portion. The handle further comprises a top entry port in fluid communication with a first lumen having a first longitudinal axis extending therethrough and a side entry port in fluid communication with a second lumen having a second longitudinal axis extending therethrough which intersects with the first longitudinal axis of the first lumen. The cannula shaft comprises an elongate body having a proximal end, a distal end, and a longitudinal axis extending therethrough. The proximal end of the elongate body extends from the distal portion of the handle body and the distal end of the elongate body terminates in a pointed tip. The channel shaft further has an inner wall defining a channel, the channel having a proximal end and a distal end. The proximal end of the channel is in fluid communication with the first and second lumens of the handle and the distal end of the channel is spaced apart from the distal end of the elongate body. The distal end of the channel is also in fluid communication with a side distal exit port. The inner wall is configured to laterally deflect the channel at its distal end with respect to the longitudinal axis of the elongate body of the cannula shaft to transition the channel's distal end to the side distal exit port. The cannula system further comprises a deflector that is selectably moveable into the first lumen of the handle through a lateral opening. The deflector has a surface that is angled or curved with respect to the first and second longitudinal axes to guide an orthopedic tool accessed through the side entry port down the second lumen of the handle.

In another embodiment, the present invention provides a method of using this embodiment of a cannula system to treat an orthopedic condition involving a target site of a patient's body. Such a method comprises inserting an orthopedic tool in the side entry port of the cannula or the top entry port of the cannula. If the orthopedic tool is inserted in the side entry port, the deflector is inserted through the lateral opening into the first lumen to act as a guide to guide the orthopedic tool down the second lumen of the handle and the channel of the cannula shaft. The method further comprises urging the orthopedic tool through the side distal exit port to access one portion of the target site. Once the orthopedic tool has exited the side distal exit port, the method comprises performing a surgical function on the one portion of the target site. In certain embodiments, only one side of the target site may need surgical intervention. However, in other embodiments, it may be desirable to perform a surgical function on another portion of the target site. In such embodiments, the method further comprises removing the orthopedic tool from the cannula, and rotating the cannula such that the side distal exit port faces the another portion of the target site. The method further comprises urging the orthopedic tool down the second lumen of the handle with the assistance of the deflector and then urging the orthopedic tool down the channel of the channel shaft. The method further comprises urging the orthopedic tool through the side distal exit port to access the another portion of the target site. Once the orthopedic tool has exited the side distal exit port, the method further comprises performing a surgical function on the another portion of the target site. The orthopedic tool can then be removed from the patient along with the cannula. If the orthopedic tool is inserted in the top entry port of the cannula, then a similar method is employed except that the orthopedic tool travels down the first lumen of the handle and no deflector is employed. This process can be repeated on as many different portions of the target site as necessary. Of course it is understood that one port can be used when performing the surgical function on one portion of the target site and another port can be used when performing the surgical function on another portion of the target site. It is also understood that one entry port can be used to deliver one type of surgical tool to perform one type of function and the other port can be used to deliver a surgical tool to perform another type of function. In a preferred embodiment, the orthopedic tool is a bone tamp, the target site is a vertebral fracture and the surgical function is tamping bone.

In another embodiment, the present invention provides a cannula system comprising a handle and a cannula shaft. The handle comprises a handle body having a proximal portion and a distal portion and further comprises a top entry port in fluid communication with a first lumen having at least a first proximal portion that is straight. The handle further comprises a side entry port in fluid communication with a second lumen having at least a first proximal portion that is curved. The cannula shaft comprises an elongate body having a proximal end, a distal end, and longitudinal axis extending therethrough. The proximal end of the elongate body depends from the distal portion of the handle body and the distal end of the elongate body terminates in a pointed tip. The cannula shaft further has an inner wall defining a channel, the channel having a proximal end and a distal end. The proximal end is in fluid communication with the first and second lumens of the handle and the distal end of the channel is in fluid communication with a side distal exit port. The distal end of the channel is also spaced apart from the distal end of the elongate body. The inner wall of the cannula shaft is configured to laterally deflect the channel at its distal end with respect to the longitudinal axis of the elongate body of the cannula shaft to transition the channel's distal end to the side distal exit port.

In another embodiment, the present invention provides a method of using this embodiment of a cannula system to treat an orthopedic condition involving a target site of a patient's body. Such a method comprises inserting an orthopedic tool in the side entry port of the cannula or the top entry port of the cannula as described with the previously mentioned embodiment. However, unlike the previously described embodiment, if the orthopedic tool is inserted in the side entry port, no deflector is needed since the intrinsic curve of the second lumen can guide the orthopedic tool down the second lumen of the handle. The method further comprises urging the orthopedic tool down the channel of the cannula shaft and through the side distal exit port to access one portion of the target site. Once the orthopedic tool has exited the side distal exit port, the method comprises performing a surgical function on the one portion of the target site. In certain embodiments, only one portion of the target site may need surgical intervention. However, in other embodiments, it may be desirable to perform the surgical function on another portion of the target site. In such embodiments, the method further comprises removing the orthopedic tool from the cannula, and rotating the cannula such that the distal port faces the another portion of the target site. The method further comprises urging the orthopedic tool down the second lumen of the handle and then urging the orthopedic tool down the channel of the channel shaft. The method further comprises urging the orthopedic tool through the side distal exit port to access the another portion of the target site. Once the orthopedic tool has exited the side distal exit port, the method further comprises performing a surgical function on the another portion side of the target site. This process can be repeated on as many different portions of the target site as necessary. The orthopedic tool can then be removed from the patient along with the cannula. If the orthopedic tool is inserted in the top entry port of the cannula then a similar method is employed except that the orthopedic tool travels down the first lumen of the handle. Of course it is understood that the orthopedic tool can be inserted through one port when performing a surgical function on one portion of the target site and inserted through another port when performing a surgical function on one portion of the target site. It is also understood that one entry port can be used to deliver one type of surgical tool to perform one type of function and the other port can be used to deliver a surgical tool to perform a different type of function. In a preferred embodiment, the orthopedic tool is a bone tamp, the target site is a vertebral fracture, and the surgical function is tamping bone.

In another embodiment, the present invention provides a cannula system including a cannula. The cannula comprises a handle and a cannula shaft. The handle comprises a handle body having a proximal portion and a distal portion. The cannula shaft comprises an elongate tubular body having a proximal end depending from the distal portion of the handle body, a distal end terminating in a pointed tip, and a longitudinal axis extending therethrough. The handle further comprises a first side entry port in fluid communication with a first lumen that has at least a partial section that is curved or angled with respect to an imaginary center line that extends through the handle body. The imaginary center line is also aligned with the longitudinal axis of the cannula shaft. The handle further comprises a second side entry port in fluid communication with a second lumen that has at least a partial section that is curved or angled with respect to an imaginary center line that extends through the handle body and that is aligned with the longitudinal axis of the cannula shaft. The cannula shaft further has a first inner wall defining a first channel. The first channel has a proximal end and a distal end. The proximal end of the first channel is in fluid communication with the first lumen of the handle body and the distal end of the first channel is in fluid communication with a first side distal exit port. The distal end of the first channel is also spaced apart from the distal end of the elongate body. The first inner wall is configured to lateral deflect the first channel at the first channel's distal end with respect to the longitudinal axis of the elongate body to transition the first channel's distal end to the first side distal exit port. The cannula shaft further has a second inner wall defining a second channel parallel to the first channel. The second channel has a proximal end and a distal end. The proximal end of the second channel is in fluid communication with the second lumen of the handle body and the distal end of the second channel in fluid communication with a second side distal exit port. The distal end of the second channel is also spaced apart from the distal end of the elongate body. The second inner wall is configured to lateral deflect the second channel at the second channel's distal end with respect to the longitudinal axis of the elongate body to transition the second channel's distal end to the second side distal exit port.

In another embodiment, the present invention provides a method of using this embodiment of a cannula system to treat an orthopedic condition in a target site of a patient's body. Such a method comprises inserting an orthopedic tool in the first side entry port of the cannula, urging the orthopedic tool down the first lumen of the handle and then the first channel of the cannula shaft and then urging the orthopedic tool through the first side distal exit port to access one portion of the target site. Once the orthopedic tool has exited the first side distal exit port, the method comprises performing a surgical function on the one portion of the target site. In certain embodiments, only one side of the target site may need to be treated. However, in other embodiments, it may be desirable to perform the surgical function on another portion of the target site. In such embodiments, the method further comprises inserting the orthopedic tool in the second side entry port of the cannula, urging the tool down the second lumen of the handle and then the second channel of the cannula shaft. The method further comprises urging the orthopedic tool through the second side distal exit port to access the another portion of the target site. Once the orthopedic tool has exited the second side distal exit port, the method further comprises performing the surgical function on the another portion of the target site. This process can be repeated on as many different portions of the target site as necessary. The orthopedic tool can then be removed from the patient along with the cannula. Of course it is understood that one side entry port can be used to deliver one type of surgical tool to perform one type of function and the other side entry port can be used to deliver a surgical tool to perform the same function or a different type of function. In a preferred embodiment, the orthopedic tool is a bone tamp, the target site is a vertebral fracture, and the surgical function is tamping bone.

BRIEF DESCRIPTION OF THE DRAWINGS

The present invention will become more fully understood from the detailed description given hereinbelow and the accompanying drawings which are given by way of illustration only, and thus are not limitative of the present invention, and wherein.

DETAILED DESCRIPTION

Figure 1:
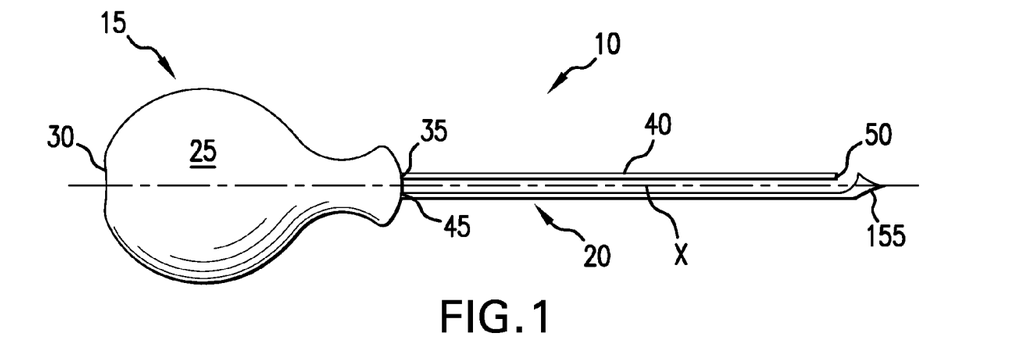
FIG. 1 is a side view of a cannula according to an embodiment of the present invention.

As used herein, the terms "side," "top" and "down" are described with respect to the cannula system as seen from a top plan view (such as shown in FIG. 1).

In general, the present invention provides a cannula system that is readily maneuverable in an operating room setting, can be used to expose different instrumentalities to a target site, and has directional capabilities to allow the user to treat multiple quadrants or areas of a target site. Since the cannula system has particular application in the orthopedic setting, the target site is often bone.

Figure 3:
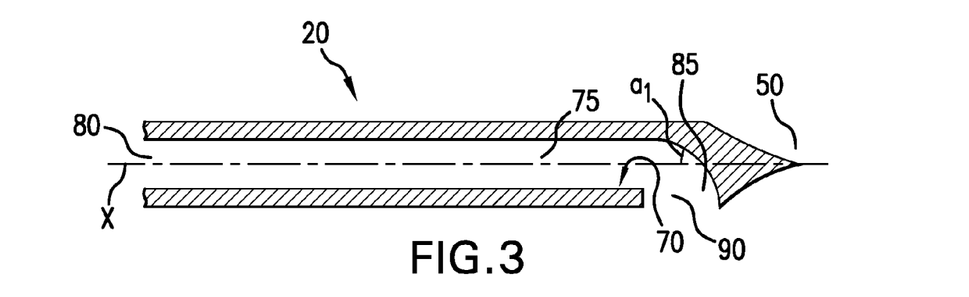
FIG. 3 is a side cross-sectional view of a cannula shaft according to an embodiment of the present invention.

Specifically, referring to FIG. 1, in an embodiment, the present invention provides a cannula system that includes a cannula 10 comprising a handle 15 and a cannula shaft 20. Handle 15 comprises a handle body 25 having a proximal portion 30 and a distal portion 35. Cannula shaft 20 comprises an elongate tubular body 40 having a proximal end 45 and a distal end 50. Proximal end 45 depends from distal portion 35 of handle body 25 and distal end 50 terminates in a tip 155. In preferred embodiments, tip 155 is a closed tip. Tip 155 can have any suitable configuration to cut into tissue such as, for example, a diamond shape, as shown in FIG. 3 or a beveled or threaded tip, the latter of which may allow for slower insertion of the cannula into bone. Elongate tubular body 40 further has a longitudinal axis X extending through proximal end 45 and distal end 50.

Figure 2:
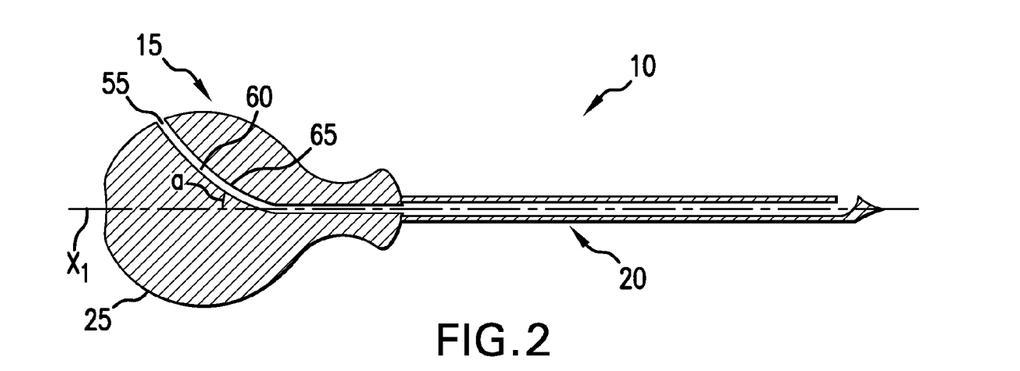
FIG. 2 is a side cross-sectional view of a cannula according to an embodiment of the present invention.

Referring to FIG. 2, in an embodiment, handle 15 further comprises a first side entry port 55 in fluid communication with a first lumen 60 that has at least a partial section 65 that is curved or angled with respect to an imaginary center line $X_1$, such center line extending through handle body 25 and being aligned with the longitudinal axis X of cannula shaft 20. In a preferred embodiment, the at least partial section 65 of first lumen 60 forms an acute angle a with respect to imaginary center line $X_1$ of handle body 25. This configuration of handle 25 allows a user to laterally insert any suitable instrumentality into first lumen 60 via first side entry port 55, which, in turn, allows the user to maneuver the device without facing any vertical height constraints that exist in prior art cannula systems where the users could only access the cannula shaft via a top entry port in the handle.

Figure 4:
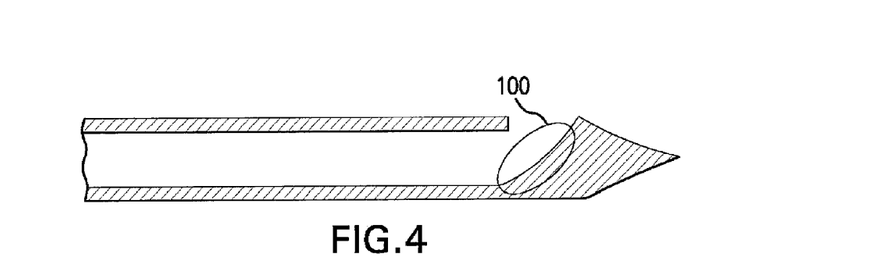
FIG. 4 is a side cross-sectional view of a cannula shaft according to an embodiment of the present invention.
Figure 5:
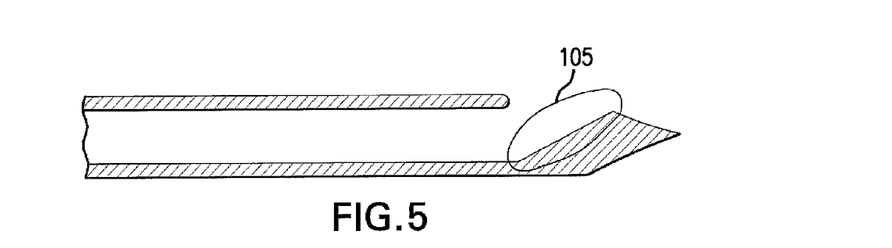
FIG. 5 is a side cross-sectional view of a cannula shaft according to an embodiment of the present invention.

Referring to FIG. 3, cannula shaft 20 of cannula 10 has an inner wall 70 defining a channel 75 that is in fluid communication with first lumen 60 of handle 15 (such first lumen and channel collectively referred to herein with respect to this embodiment as a bore). Channel 75 has a proximal end 80 and a distal end 85. Proximal end 80 is adjacent to and in fluid communication with first lumen 60 of handle body 25 and distal end 85 is adjacent to and in fluid communication with a first side distal exit port 90. Distal end 85 of channel 75 is also spaced apart from distal end 50 of elongate body 40 of cannula shaft 20. As seen in FIG. 3, inner wall 70 is configured to laterally defect channel 75 at the channel's distal end 85 with respect to longitudinal axis X of elongate body 40. Therefore, inner wall 70 has a curvature 100, as more clearly seen in FIG. 4 or an angled portion 105, as more clearly seen in FIG. 5, to transition channel 75 to first side distal exit port 90. Referring back to FIG. 3, preferably distal end 85 of channel 75 forms an acute angle $a_1$ with respect to longitudinal axis X of elongate body 40.

This side distal exit port of cannula shaft 20 allows a user to insert an instrument through the bore to access one side of a target site of the body, such as a fractured vertebra. Upon performance of a designated procedure with the instrument, the user simply needs to remove the instrument, rotate the cannula a desired degree to access another side of the target site of the body, re-insert the instrument through the bore, and perform the designated procedure with the instrument on the another side of the target site. This side distal exit port provides a user with directionality during the procedure so that the user can access different areas of the target site.

Figure 6:
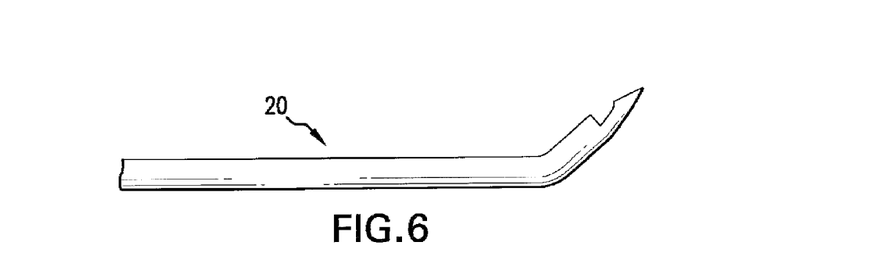
FIG. 6 is a side view of a cannula according to an embodiment of the present invention.

Referring to FIG. 6, in certain embodiments, cannula shaft 20 is pre-bent near its distal end to provide an additional degree of directionality.

Figure 7:
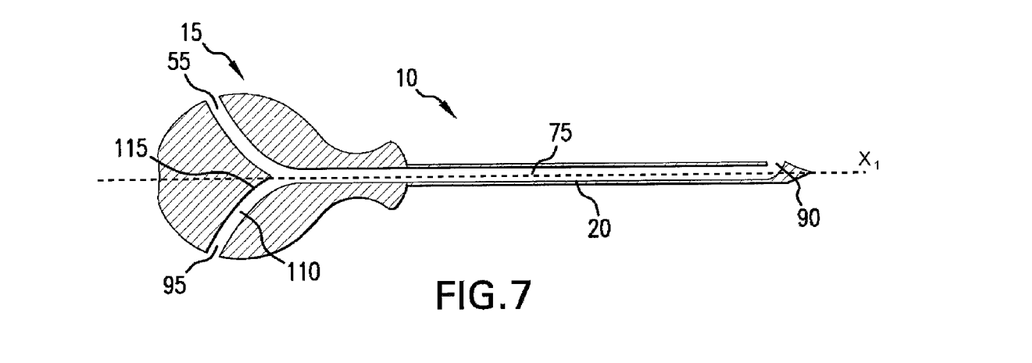
FIG. 7 is a side cross-sectional view of a cannula shaft according to an embodiment of the present invention.

Referring to FIG. 7, in another embodiment, the present invention provides a cannula system including a cannula 10 where handle 15 further comprises a second side entry port 95 on an opposite side of handle body 15 than first side entry port 55. Second side entry port 95 is in fluid communication with a second lumen 110 that has at least a partial section 115 that is curved or angled with respect to an imaginary center line $X_1$, such center line extending through handle body 25 and being aligned with the longitudinal axis X of cannula shaft 20. Furthermore, second lumen 110 is in fluid communication with channel 75 of cannula shaft 20 (such second lumen and channel referred to herein with respect to this embodiment as a bore). Channel 75, in turn, is in fluid communication with side distal exit port 90. Such a design allows a user to insert an instrument through either first or second side entry port depending, for example, on which side is more accessible or comfortable for the user. Alternatively, such a design allows a user to insert one type of instrument through the first entry port and another type of instrument through the second entry port.

Figure 8:
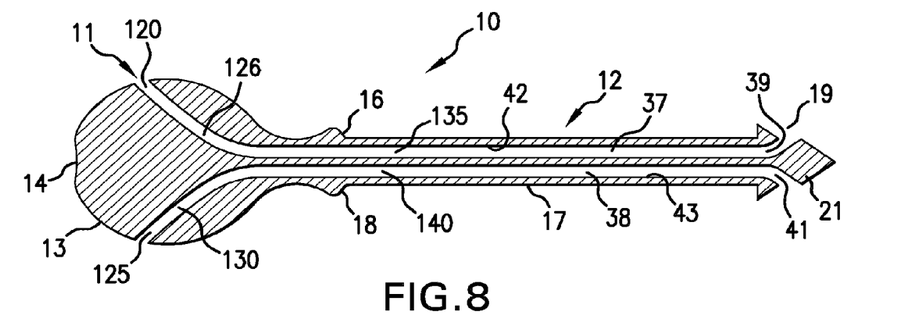
FIG. 8 is a side cross-sectional view of a cannula shaft according to an embodiment of the present invention.
Figure 9:
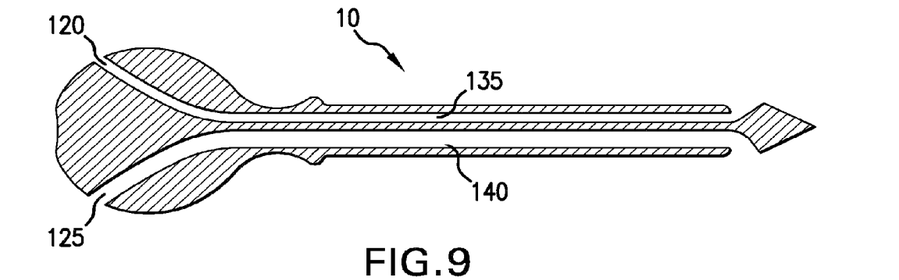
FIG. 9 is a side cross-sectional view of a cannula shaft according to an embodiment of the present invention.

Referring to FIG. 8, in another embodiment, the present invention provides a cannula system including a cannula with dual lumens. Specifically, in this embodiment, cannula 10 comprises a handle 11 and a cannula shaft 12. Handle 11 comprises a handle body 13 having a proximal portion 14 and a distal portion 16. Cannula shaft 12 comprises an elongate tubular body 17 having a proximal end 18 and a distal end 19. Proximal end 18 depends from distal portion 16 of handle body 13 and a distal end 19 terminates in a pointed tip 21. Handle 11 comprises a first side entry port 120 on one side of handle body 13 and a second side entry port 125 on an opposite side of handle body 13. As with the embodiment described with respect to FIG. 7, first side entry port 120 is in fluid communication with a first lumen 126 that has at least a partial section that is curved or angled and second side port 125 is in fluid communication with a second lumen 130 that has at least a partial section that is curved or angled. However, unlike FIG. 7, first and second lumens 126 and 130 are in fluid communication with separate, parallel first and second channels 135 and 140, respectively, of cannula shaft 12 (such first lumen 126 and first channel 135 collectively referred to herein with respect to this embodiment as a first bore and such second lumen 130 and second channel 140 collectively referred to as a second bore). In the embodiment illustrated in FIG. 8, the first and second bores 37 and 38 have the same general diameter. However, in other embodiments, it may be preferable for one of the bores to be larger than the other bore as illustrated in FIG. 9.

First channel 135 of cannula shaft 12 is defined by a first inner wall 42 and is in fluid communication with and adjacent to first lumen 126 of handle body 13 at one end, as stated above, and in fluid communication with and adjacent to a first side distal exit port 39 at another end. Similarly, second channel 140 is defined by a second inner wall 43 and is in fluid communication with second lumen 130 at one end, as stated above, and in fluid communication with a second side distal exit port 41 at another end. As seen in FIG. 8, first and second inner walls 42 and 43 are configured to laterally defect respective channels 135 and 140 at the respective channel's distal end with respect to longitudinal axis X of elongate body 17 to transition the respective channels to the respective side distal exit ports.

The opposing side distal exit ports of cannula shaft 12 in this embodiment allows a user to insert an instrument through the first bore of cannula 10 to access one side of a target site of the body, such as a fractured vertebra. Upon performance of a designated procedure with the instrument, the user need not rotate the cannula to access the opposing side of the target site. Rather, the user simply needs to insert the same instrument or an identical instrument through the second bore to access the opposing side of the target site. Alternatively or in addition, the user can use the first and second side ports 125 and 120 to insert different types of instrumentalities.

Figure 10:
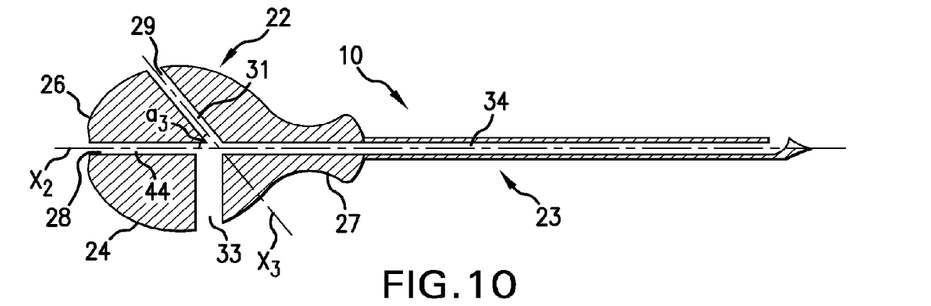
FIG. 10 is a side cross-sectional view of a cannula shaft according to an embodiment of the present invention.
Figure 11:
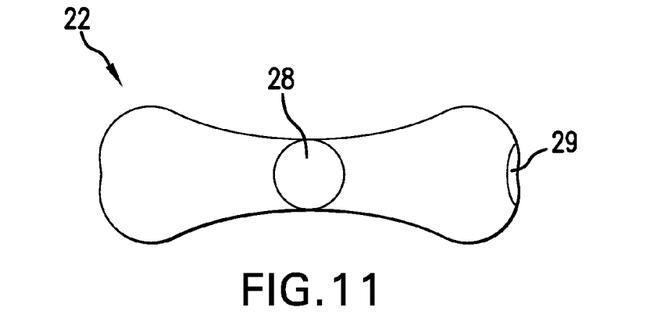
FIG. 11 is a top view of a handle of a cannula according to an embodiment of the present invention.

Referring to FIG. 10, in another embodiment, the present invention provides a cannula system including cannula 10 comprising a handle 22 and a cannula shaft 23. Handle 22 comprises a handle body 24 having a proximal portion 26 and a distal portion 27. The handle further comprises a top entry port 28 in fluid communication with a first lumen 44 having a first longitudinal axis $X_2$ extending therethrough. Handle 22 further comprises a side entry port 29 in fluid communication with a second lumen 31 having a second longitudinal axis $X_3$ extending therethrough which intersects with the first longitudinal axis $X_2$ of first lumen 44. FIG. 11 provides a top plan view of handle 22 to illustrate the location of top entry port 28 and side entry port 29 in this embodiment. Preferably, second longitudinal axis $X_3$ intersects with first longitudinal axis $X_2$ at an angle, $a_3$ of 90° or less.

Figure 12:
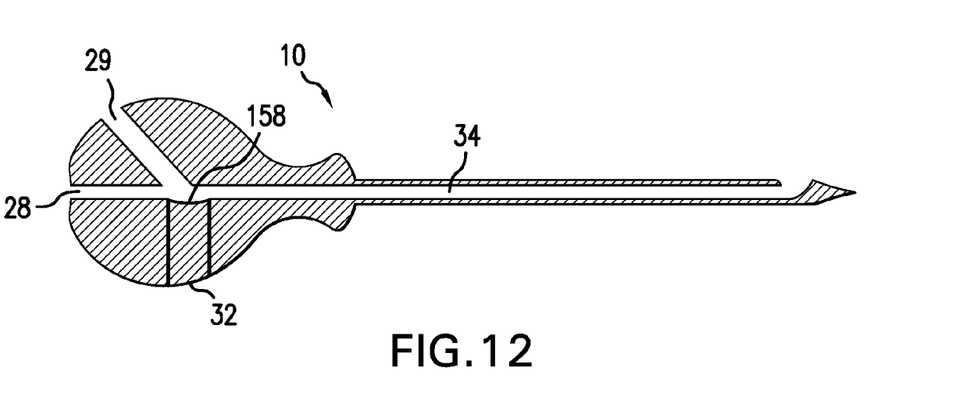
FIG. 12 is a side cross-sectional view of a cannula shaft according to an embodiment of the present invention with a deflector inserted into a lateral opening of the handle.

Referring to FIG. 12, the cannula system further comprise a deflector 32 that is selectively moveable into first lumen 44 through a lateral opening 33 (shown also in FIG. 10). Deflector 32 has a surface 158 that is angled or curved with respect to first and second longitudinal axes $X_2$ and $X_3$. Referring back to FIG. 10, cannula shaft 23 is configured as described with respect to FIG. 2 such that a channel 34 of cannula shaft 23 is in fluid communication with first and second lumens 44 and 31 of handle 22 (such channel and first lumen collectively referred to herein as a first bore and such channel and second lumen collectively referred to as a second bore for purposes of this embodiment). In such an embodiment, the user has a choice whether to use the top entry port, as is done conventionally, to insert an instrument through the cannula or to use the side entry port, as described above. If the user decides to use side entry port 29, then the user can insert deflector 32 into lateral opening 33 so that the angled or curved surface 158 of the deflector can guide the instrument down channel 34.

Figure 13:
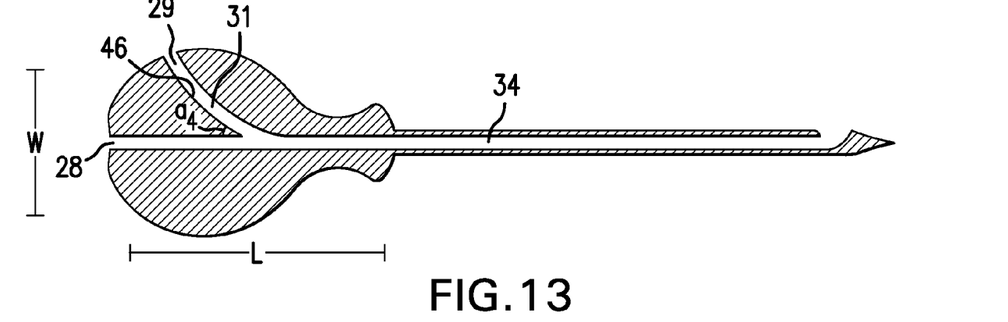
FIG. 13 is a side cross-sectional view of a cannula shaft according to an embodiment of the present invention.

Referring to FIG. 13, in another embodiment, cannula 10 can be designed to avoid the need for a deflector. For example, second lumen 31 can be defined by an inner wall 46 that has a curvature sufficient to inherently guide an instrument down lumen 31 to channel 34. Specifically, an instrument will follow the arc of inner wall 46 to channel 34. Preferably, the angle $a_4$ is 45° or less.

Regarding exemplary measurements of a cannula according to embodiments of the present invention, in certain embodiments, the handle has a length L of between about 4 to 5 inches, preferably about 2 to 3 inches. In certain embodiments, the handle has a width W, as measured at its maximum width, of between about 0.25 inches to 0.50 inches. In certain embodiments, cannula shaft has length between about 4 and 8 inches, preferably about 6 inches and a diameter of about 11 to 17 gauge, and preferably about 13 gauge.

The above described cannula be used with a variety of different instruments to perform various functionalities. For example, a cannula can be used with a bone tamp to provide a mechanical means by which to lift or elevate bone to reduce a bone fracture, for example. An exemplary illustration of a bone tamp device 47 is provided in FIG. 14. This bone tamp device comprises a rod 48 depending from a handle 49. Rod 48 has a length longer than that of any of the bores of a cannula so that, in use, rod 48 can extend past the side distal exit port of the cannula to access the target site. Preferably, handle 49 has a flattened configuration for ease of manipulation during use. In embodiments where bone tamp device 47 is inserted in a side curved or angled lumen (as described above), rod 48 is fabricated from a flexible material to allow rod 48 to bend as it is urged down the curved or angled lumen. Non-limiting examples of suitable flexible materials include a flexible metal or elastomeric polymer. Non-limiting examples of suitable materials include titanium, expandable polytetrafluorethylene (ePTFE), or polyetheretherketone (PEEK).

Figure 14:
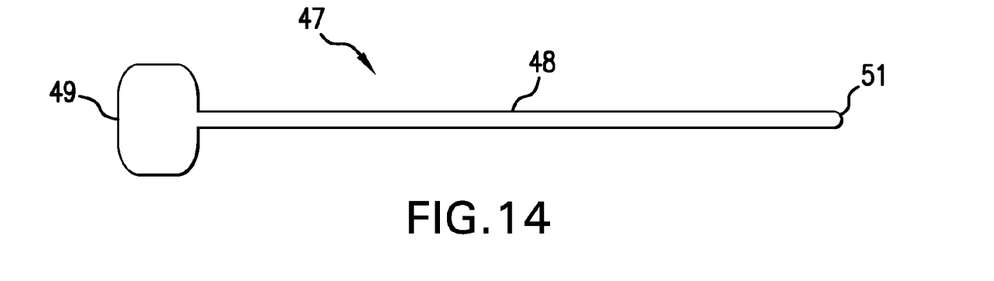
FIG. 14 is a perspective view of a bone tamp device according to an embodiment of the present invention.

The distal end tip 51 of rod 48 is shown in FIG. 14 as being rounded. However, the tip could be flat, sharp, threaded or have other configurations so long as the bone tamp can be used to elevate bone. The other configurations of distal end tip 51 could also be tailored to match other functionalities for which the bone tamp may be used. For example, bone tamp device 47 could be used as an osteotome, for example, to cut a sclerotic lesion that otherwise prevents the bone tamp from elevating the rest of the bone. In such an embodiment, it may be desirable for the distal end of the bone tamp device to be sharp although this is not a necessity. To use the bone tamp device as an osteotome, the bone tamp can be inserted into a bore of a cannula and, upon reaching the site that is to be cut, urged out of a side distal exit port of the cannula at a distance, for example, of three to four millimeters. In order to cut the desired tissue, the handle of the cannula and the handle of the bone tamp device can be turned in concert causing the cannula and bone tamp to rotate, thereby allowing the bone tamp to cut the desired tissue.

In alternative embodiments, the bone tamp is not used as the osteotome, but rather a separate osteotome is used.

Figure 15:
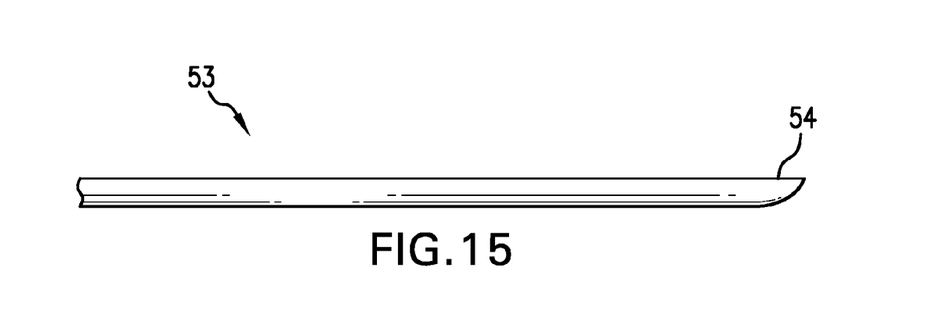
FIG. 15 is a side view of a stylet according to an embodiment of the present invention.

In addition or alternatively, the cannula can be used with or as a biopsy needle to aspirate fluid from the bone tissue and/or to retrieve bone marrow tissue itself. For this use, a stylet 53 with a sharp tip, as shown in FIG. 15, can be inserted into any of the above described bores of a cannula and urged through a side distal exit port of the shaft. Upon entering the bone marrow cavity, the stylet can be withdrawn and, using a syringe at the proximal end of the cannula (through either a top or side port), marrow can be aspirated under negative pressure. If it is desired to also retrieve a solid bone marrow specimen, then a cylindrical tube can be inserted into another bore of the cannula. In such a case, it is desirable for the another bore in which the cylindrical tube is inserted to be larger than the bore used to aspirate fluid from the bone marrow so that the larger bore can accommodate a larger diameter cylindrical tube. Such a configuration of a cannula where one bore is larger than another bore is shown in FIG. 9. Once the larger diameter cylindrical tube is positioned in the cannula, a stylet can be used to penetrate the bone cortex. The stylet can then be withdrawn and the larger diameter tube remaining in the another bore can be pushed further into the marrow causing a core of marrow to enter the tube. The tube can then withdrawn from the cannula and the core of marrow pushed out with a blunt probe through the tube lumen.

In the embodiment shown in FIG. 15, the distal end 54 of stylet 53 is shaped to match the curvature of the distal end of a cannula shaft of a cannula to fill the side distal exit port. Such a configuration may be useful to prevent debris from entering the cannula and also to increase the strength of the cannula so that the cannula will not bend when pressure is applied thereto (such as in the case of hammering the cannula) in certain circumstances. Of course, other shapes for the distal end of the stylet could also be used.

In addition or alternatively, a cannula of the present invention can be used to deliver a bone material to a bone fracture site in order to augment the bone. The bone material can be a bone graft material, a bone paste and/or a bone morphogenetic protein (BMP). Bone graft materials are well known in the art and include both natural and synthetic materials. For example, the bone graft material can be an autologous or autograft, allograft, xenograft, or synthetic bone graft. The bone graft can be in the form of corticocancellous bone chips. BMPs are also well known in the art and include BMP-2, BMP-3, BMP-4, BMP-5, BMP-6 (VGR-1), BMP-7 (OP-1), BMP-8, BMP-9, BMP-10, BMP-1, BMP-12, BMP-13, BMP-14, BMP-15. Preferred BMPs are any of BMP-2, BMP- 3, BMP-4, BMP-5, BMP-6, and BMP-7. The bone paste can be a cement or ceramic material including, for example, polymethylmethacrylate. The bone material can be introduced through any of the above described entry ports of the cannulas of the present invention via mechanisms known in the art, such as syringes and filler tubes that are attachable or otherwise able to be received by the entry ports.

Figure 16:
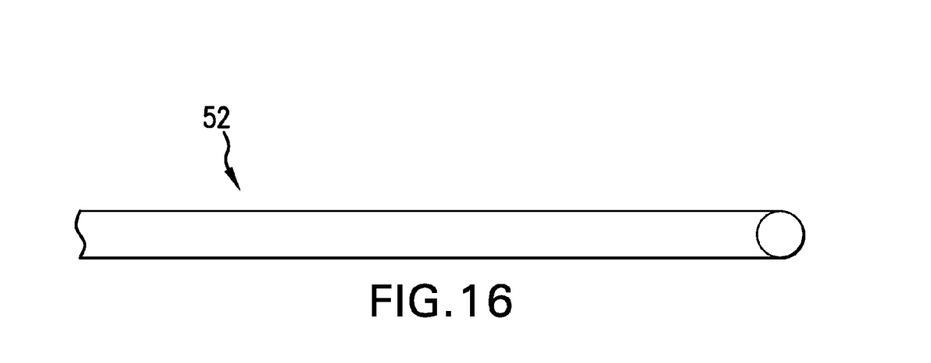
FIG. 16 is a side view of a catheter according to an embodiment of the present invention.

In addition or alternatively, a cannula of the present invention can be used with a catheter 52 as shown in FIG. 16 to deliver a therapeutic agent to a target site. Non-limiting examples of therapeutic agents include anti-microbial agents, antibiotics or stem cells. Such therapeutic agents can be delivered separately to the target site or can be incorporated into a bone material (described above) and delivered to the target site.

In addition or alternatively, a cannula of the present invention can be used to deliver a viscoelastic polymer to a disc to replace other components of the disc, such as the nucleus pulposis.

A cannula of the present invention can be used with other type of orthopedic tools used in spinal surgery such as devices that deliver thermal or heat energy including radiofrequency waves and/or laser beams. The cannulas could also be used to delivery non-thermal energy such as low energy radiofrequency waves for plasma disc decompression. Specifically, the cannulas of the present invention can be used to deliver radio wave signals through an electrode introduced into a bore of the cannula to the nucleus pulposus. The radio waves produce a low-temperature ionized gas or plasma that breaks up molecular bonds in the nucleus, removing tissue volume, which results in disc decompression.

Any of the above-described processes and tools can be used with any of the other above-described processes and tools in cannula systems of the present invention. Further, other orthopedic tools used in orthopedic surgeries could be used in addition to or as an alternate to the above-described orthopedic tools.

The systems and methods of the present invention can be used in a variety of orthopedic procedures to treat a variety of orthopedic conditions. For example, the systems of the present invention can be used procedures such as disc decompression, discectomy, stabilization (fusion), kyphoplasty and vertebroplasty. In a preferred embodiment, the systems of the present invention are used to treat fractures. The fractures can be in various parts of the body, such as fractures of the shoulder, arms, wrists, hands and fingers; fractures of the spine; fractures of the hips and pelvis; and fractures of the legs, knees and feet. In a particularly preferred embodiment, the systems and methods of the present invention are used to treat vertebral fractures. Such vertebral fractures (as well as other spine conditions that can be addressed by a cannula system of the present invention) can be caused by a variety of etiologies such as, for example, scoliosis, herniated disc, spondylolisthesis, sciatica, spondylitis, spondylosis, spinal stenosis, trauma, tumor reconstruction or degenerative disc diseases. Of course the above listed conditions and etiologies are only exemplary and the systems of the present invention are not necessarily limited to any particular use.

Preferably, the systems of the present invention access the fractures via a minimally invasive route, such as percutaneously. In embodiments where the fracture that is treated is a spinal fracture, the systems can access the spine through various approaches such as a posterior approach or an anterior approach.

Figure 17:
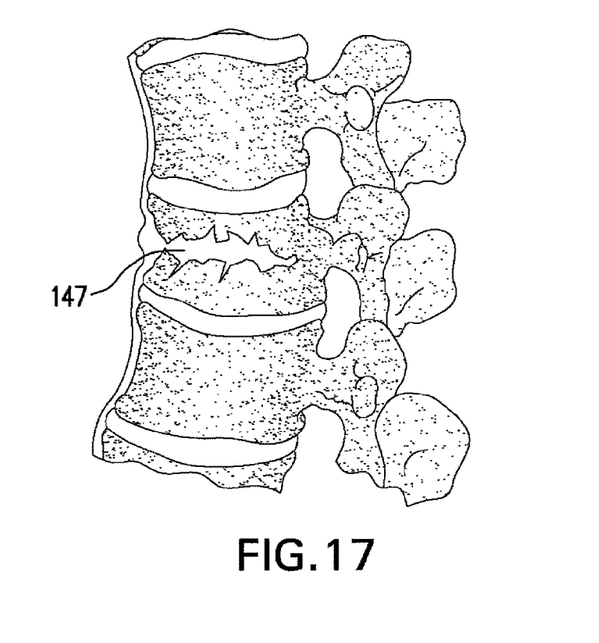
FIG. 17 is a schematic illustration of a fractured vertebra.

An exemplary surgical procedure will now be described using a cannula system of the present invention for vertebral body fracture reduction on a patient with a collapsed vertebral body, as shown in FIG. 17, who is in need of reduction of fracture 147 followed by filling in of the void created by such reduction. Under general anesthesia, the patient is positioned prone on a radiolucent operating table and biplanar fluoroscopy is used to visualize the fractured vertebral body. A stylet is inserted into a cannula 10 of the present invention and the cannula is inserted into the body in a percutaneous fashion to the level of the pedicle or any other desired position on the vertebral body. This process is followed fluoroscopically to ensure proper positioning of the cannula. Once the cannula is inserted to the desired location in the vertebral body, the stylet can be removed and a biopsy can be obtained by removing the cannula stylet and inserting a plastic or metal cylindrical tube with an auger type end into the bone to retrieve a desired sample. This same procedure can be repeated on the contralateral side of the vertebral body if desired or needed.

Figure 18:
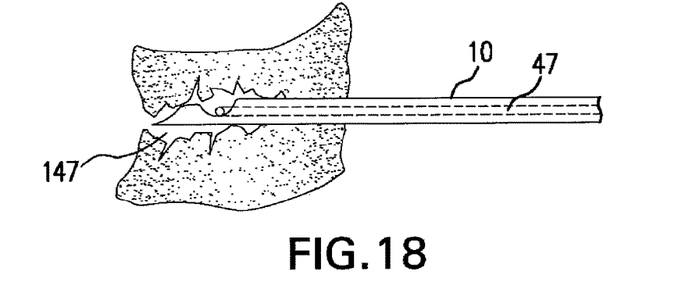
FIG. 18 is a schematic illustration of a cannula carrying a bone tamp according to an embodiment of the present invention inserted into the fractured vertebra of FIG. 17.
Figure 19:
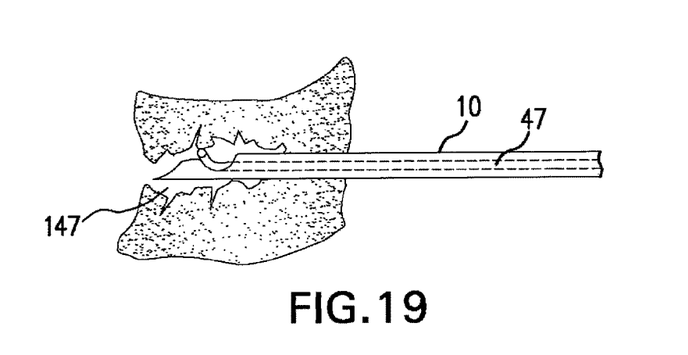
FIG. 19 is a schematic illustration of the bone tamp device of FIG. 18 that has exited a side distal exit port of the cannula to tamp one side of the vertebra.
Figure 20:
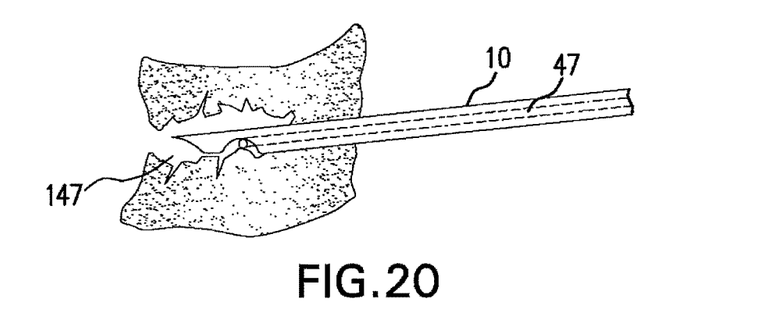
FIG. 20 is a schematic illustration of the cannula of FIG. 18 rotated 180°.
Figure 21:
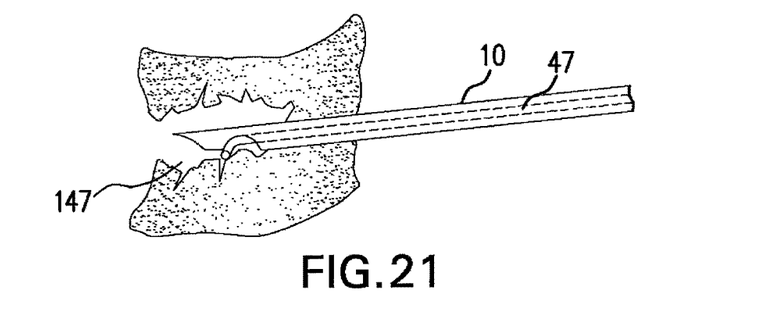
FIG. 21 is a schematic illustration of the cannula of FIG. 20 where the bone tamp has exited the side distal exit port of the cannula to tamp the opposing side of the vertebra.

To perform reduction of the vertebral body, a bone tamp device 47 is inserted into the cannula as shown in FIG. 18. As shown in FIG. 19, tamp device 47 is deflected by the angled or curved side distal exit port of the cannula and becomes directional by means of turning the cannula handle, which can have directional markings on the handle. By withdrawing and inserting the inner device multiple times, the tamp can be used to reduce the compressed vertebral bone and this reduction can be observed by means of fluoroscopy. The directional capability of the cannula will allow for reduction of multiple quadrants or areas of the vertebral body. For example, as shown in FIGS. 20 and 21, the cannula can be rotated to tamp the opposing side of fracture 147.

The reduction procedure can create small voids that can be stabilized with cement or other materials capable of hardening or at least forming a stable construct onto which the fracture reduction can rest. In such an instance, a high viscosity bone cement is inserted into the vertebral body via the cannula. The bone tamp device and stylet are removed from the cannulas and the bone cement attachments are attached to the entry ports. This will allow directional placement of cement into the vertebral bodies at a slow rate with cement that is highly viscous thus allowing for visualization under fluoroscopy (as the cement would be radio opaque). After the cement is injected, the cannula is rotated to break any remaining cement ties with the cannula and then the cannula is withdrawn.

The foregoing description and examples have been set forth merely to illustrate the invention and are not intended as being limiting. Each of the disclosed aspects and embodiments of the present invention may be considered individually or in combination with other aspects, embodiments, and variations of the invention. Further, while certain features of embodiments of the present invention may be shown in only certain figures, such features can be incorporated into other embodiments shown in other figures while remaining within the scope of the present invention. In addition, unless otherwise specified, none of the steps of the methods of the present invention are confined to any particular order of performance. Modifications of the disclosed embodiments incorporating the spirit and substance of the invention may occur to persons skilled in the art and such modifications are within the scope of the present invention. Furthermore, all references cited herein are incorporated by reference in their entirety.

What is claimed is:

1. A cannula system comprising:
   a cannula comprising:
      a handle and a cannula shaft, the handle comprising a handle body having a proximal portion and a distal portion, the cannula shaft comprising an elongate tubular body having a proximal end depending from the distal portion of the handle body, a distal end terminating in a pointed tip, and a longitudinal axis extending therethrough, the handle further comprising a first entry port in fluid communication with a first lumen, the cannula shaft further having an inner wall defining a first channel, the first channel having a proximal end and a distal end, the proximal end of the first channel in fluid communication with the first lumen of the handle body, the distal end of the first channel in fluid communication with a first side distal exit port and spaced apart from the distal end of the elongate body, at least a portion of the inner wall adjacent the first side distal exit port configured to laterally deflect the first channel at the first channel's distal end with respect to the longitudinal axis of the elongate body to transition the first channel's distal end to the first side distal exit port; and a bone tamp comprising a rod having a distal end, at least a portion sufficiently flexible for the distal end of the rod to extend out of the first side distal exit port when the rod is inserted in the first entry port to a length greater than a distance between the first entry port and the first side distal exit port.

2. The cannula system of claim 1, wherein the distal end of the first channel forms an acute angle with respect to the longitudinal axis of the elongate body.

3. The cannula system of claim 1, further comprising an orthopedic surgical tool sized to be inserted into the first side entry port of the handle and the channel of the cannula shaft.

4. The cannula system of claim 3, wherein the orthopedic surgical tool is selected from the group consisting of a biopsy tube, a stylet, an electrode, a drug delivery catheter, an osteotome, or any combination thereof.

5. The cannula system of claim 1, further comprising a bone material insertable into the first side entry port of the handle and the channel of the cannula shaft.

6. The cannula system of claim 5, wherein the bone material is a bone cement or bone paste.

7. The cannula system of claim 1, further comprising means for introducing a bone material into the cannula, the means attachable to the first side entry port.

8. A method of reducing a fracture in a bone comprising:
providing the cannula system of claim 1;
inserting the bone tamp in the side entry port;
urging the bone tamp device down the first lumen of the handle and then the first channel of the cannula shaft;
urging the bone tamp device through the first side distal exit port to access one side of the fracture; and
tamping the bone on the one side of the fracture to elevate the bone.

9. The method of claim 8, further comprising:
removing the bone tamp device from the cannula;
rotating the cannula such that the first side distal exit port faces an opposing side of the fracture;
re-inserting the bone tamp device in the first side distal exit port;
urging the bone tamp device down the first lumen of the handle and then the first channel of the cannula shaft;
urging the bone tamp device through the first side distal exit port to access an opposing side of the fracture; and
tamping the bone on the opposing side of the fracture to elevate the bone.

10. A method of creating a void in a bone comprising:
providing the cannula system of claim 1;
inserting the bone tamp in the side entry port;
urging the bone tamp device down the first lumen of the handle and then the first channel of the cannula shaft;
urging the bone tamp device further down the first lumen of the handle until the distal end of the rod extends out of the first side distal exit port to access a portion of said bone; and
tamping the bone with at least the portion of the rod extending out of the first side distal exit port to create a void in the bone.

11. The method of claim 10, further comprising:
removing the bone tamp device from the cannula; and
injecting cement through the cannula shaft and into said void.

12. The cannula system of claim 1, wherein the first side entry port is offset with respect to an imaginary center line that extends through the handle body and is aligned with the longitudinal axis of the cannula shaft, the first lumen being curved or angled with respect to the imaginary center line.

13. The cannula system of claim 1, wherein the portion of the inner wall is configured to deflect the distal end of the rod through the first side distal exit port when the rod is inserted into the first entry port to the length greater than the distance.

14. The cannula system of claim 1, wherein the distal end of the rod is rounded.

15. The cannula system of claim 1, wherein the rod does not have any radially expandable portions.

16. A cannula system comprising:
a cannula comprising a handle and a cannula shaft, the handle comprising a handle body having a proximal portion and a distal portion and further comprising: a top entry port in fluid communication with a first lumen having a first longitudinal axis extending therethrough;
a side entry port in fluid communication with a second lumen having a second longitudinal axis extending therethrough which intersects with the first longitudinal axis of the first lumen; and
the cannula shaft comprising an elongate body having a proximal end, a distal end, and a longitudinal axis extending therethrough, the proximal end of the elongate body depending from the distal portion of the handle body and the distal end of the elongate body terminating in a pointed tip, the elongate body further having:
an inner wall defining a channel, the channel having a proximal end and a distal end, the proximal end in fluid communication with the first and second lumens of the handle and the distal end of the channel in fluid communication with a side distal exit port, the distal end of the channel spaced apart from the distal end of the elongate body, the inner wall configured to laterally deflect the channel at its distal end with respect to the longitudinal axis of the elongate body of the cannula shaft to transition the channel's distal end to the side distal exit port; and
a deflector that is removably received in a lateral opening, wherein a distal end of the deflector extends into the first lumen, and the distal end of the deflector has a surface that is angled or curved with respect to the first and second longitudinal axes.

17. The cannula system of claim 16, further comprising an orthopedic surgical tool sized to be inserted into the top entry port and the side entry port of the handle and the channel of the cannula shaft.

18. The cannula system of claim 17, wherein the orthopedic surgical tool is selected from the group consisting of a bone tamp device, a biopsy tube, a stylet, an electrode, a drug delivery catheter, an osteotome, or any combination thereof.

19. The cannula system of claim 16, further comprising a bone material insertable into the first entry port or the top entry port of the handle and the channel of the cannula shaft.

20. The cannula system of claim 19, wherein the bone material is a bone cement or bone paste.

21. A method of using the cannula system of claim 16 to treat an orthopedic condition comprising:
using the cannula system of claim 16;
inserting an orthopedic tool in the side entry port of the handle;
inserting the deflector in the lateral opening of the handle;
  urging the orthopedic tool against an angled or curved surface of the deflector to deflect the orthopedic tool down the second lumen of the handle and the channel of the cannula shaft;
  urging the orthopedic tool through the side distal exit port to access one portion of the target site in the body; and
performing a surgical function on the one portion of the target site.

22. A method of reducing a fracture in a bone comprising:
providing the cannula system of claim 16;
inserting a bone tamp device in the side entry port;
inserting the deflector in the lateral opening of the handle;
urging the bone tamp device against an angled or curved surface of the deflector to deflect the bone tamp device down the second lumen of the handle and then the channel of the cannula shaft;
urging the bone tamp device through the side distal exit port to access one side of the fracture; and
tamping the bone on the one side of the fracture to elevate the bone.

23. The method of claim 16, further comprising:
removing the bone tamp device from the cannula;
rotating the cannula such that the side distal exit port faces an opposing side of the fracture;
re-inserting the bone tamp device in the side distal exit port;
re-inserting the deflector in the lateral opening of the handle;
urging the bone tamp device against the angled or curved surface of the deflector to deflect the bone tamp device down the second lumen of the handle and then the channel of the cannula shaft;
urging the bone tamp device through the side distal exit port to access an opposing side of the fracture; and
tamping the bone on the opposing side of the fracture to elevate the bone.

24. A cannula system comprising:
a cannula comprising:
  a handle and a cannula shaft, the handle comprising a handle body having a proximal portion and a distal portion, the cannula shaft comprising an elongate tubular body having a proximal end depending from the distal portion of the handle body, a distal end terminating in a pointed tip, and a longitudinal axis extending therethrough,
  the handle further comprising a first entry port in fluid communication with a first lumen,
  the cannula shaft further having an inner wall defining a first channel, the first channel having a proximal end and a distal end, the proximal end of the first channel in fluid communication with the first lumen of the handle body, the distal end of the first channel in fluid communication with a first side distal exit port and spaced apart from the distal end of the elongate body,
a bone tamp comprising a flexible rod having a distal end; and
  means for urging the distal end of the rod through the first side distal exit port when the rod is inserted in the first entry port a length greater than a distance between said first entry port and said first side distal exit port and for applying pressure with the distal end of the rod to bone adjacent the side distal port.

* * * * *